(12) United States Patent
Mangion

(10) Patent No.: US 8,071,808 B2
(45) Date of Patent: Dec. 6, 2011

(54) PROCESSES FOR PREPARING A SUBSTITUTED GAMMA-AMINO ACID

(75) Inventor: Bernardino Mangion, Santa Lucia (MT)

(73) Assignee: Laboratorio Chimico Internazionale S.p.A., Milan (IT)

( * ) Notice: Subject to any disclaimer, the term of this patent is extended or adjusted under 35 U.S.C. 154(b) by 41 days.

(21) Appl. No.: 12/745,413

(22) PCT Filed: Nov. 25, 2008

(86) PCT No.: PCT/IB2008/003232
§ 371 (c)(1), (2), (4) Date: Jun. 16, 2010

(87) PCT Pub. No.: WO2009/068967
PCT Pub. Date: Jun. 4, 2009

(65) Prior Publication Data
US 2010/0305359 A1     Dec. 2, 2010

Related U.S. Application Data

(60) Provisional application No. 61/004,982, filed on Nov. 30, 2007.

(51) Int. Cl.
*C07C 229/08* (2006.01)
(52) U.S. Cl. ...................................................... 562/553
(58) Field of Classification Search ........................ None
See application file for complete search history.

(56) References Cited

FOREIGN PATENT DOCUMENTS

WO      WO 96/38405 A1     12/1996
WO      WO 2006/122255 A1  11/2006

OTHER PUBLICATIONS

Hoekstra, Marvin et al., "Chemical Development of CI-1008, an Enantiomerically Pure Anticonvulsant," *Organic Process, Research & Development*, vol. 1, No. 1, Jan. 1, 1997, pp. 26-38.

*Primary Examiner* — Paul A Zucker
(74) *Attorney, Agent, or Firm* — Nixon & Vanderhye P.C.

(57) ABSTRACT

The present invention is related to processes suitable for industrial synthesis of pregabalin from (R)-(−)-3-(carbamoylmethyl)-5-methylhexanoic using sodium hypochlorite as described herein. In addition, the present invention is related to pregabalin which is substantially free of impurities and pharmaceutical compositions comprising pregabalin.

13 Claims, No Drawings

PROCESSES FOR PREPARING A SUBSTITUTED GAMMA-AMINO ACID

BACKGROUND OF THE INVENTION

Pregabalin, a compound of Formula I, is the international commonly accepted name for (S)-(+)-3-aminomethyl-5-methyl-1-hexanoic acid and has an empirical formula of $C_8H_{17}NO_2$. Pregabalin is also known as (S)-(+)-3-(2-methylpropyl)-4-aminobutanoic acid or (S)-(+)-3-isobutyl-GABA. Pregabalin is a commercially marketed pharmaceutically active substance known to be useful as therapeutic agent for treatment of pain, convulsions, general anxiety related disorders and epilectic seizures.

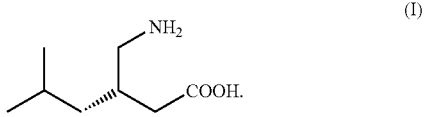

Pregabalin and its pharmaceutically acceptable salts are described in U.S. Pat. No. 6,197,819 ("the '819 patent"), along with two different synthetic processes for their preparation. However, these routes involve expensive and/or difficult to handle substances such as (4R,5S)-4-methyl-5-phenyl-2-oxazolidinone, n-butyllithium, and "azide" intermediates. The '819 patent is incorporated herein by reference.

Several patents and published patent applications (e.g, U.S. Pat. No. 5,616,793 ("the '793 patent") and International Publication Nos. WO 2006/122258 ("the '258 publication"), WO 2006/122255 ("the '255 publication"), and WO 2006/121557 ("the 557 publication")) disclose a more convenient preparation of pregabalin by means of a Hofmann rearrangement of (R)-(−)-3-(carbamoylmethyl)-5-methylhexanoic acid, a compound of Formula II, in the presence of bromine and an alkali hydroxide as depicted in Scheme 1.

The '793 patent and the '258, '255, and '557 publications are incorporated herein by reference.

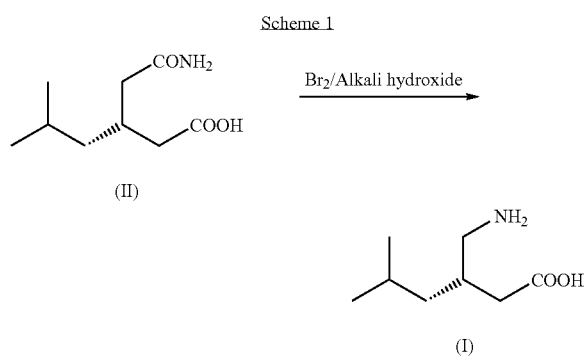

However, this synthetic method is not desirable for industrial implementation, since it requires the use of bromine, which is very toxic and corrosive. Moreover, this process involves the formation of undesired by-products. In this regard, it is well-known that the presence of impurities may adversely affect the safety and shelf life of pharmaceutical formulations.

Regarding the synthetic process described in Scheme 1 (i.e., the preparation of pregabalin via a Hofmann rearrangement reaction of a compound of Formula II), Hoekstra et al. in *Organic Process Research & Development* 1997, 1, 26-38, report that the use of sodium hypochlorite as an alternative to bromine gives poor conversions.

In view of the foregoing, there is a need to provide improved processes for preparing pregabalin which are suitable for industrial implementation, which avoid the use of bromine and which produce pregabalin substantially free of impurities.

BRIEF SUMMARY OF THE INVENTION

The present invention provides processes for preparing a compound of Formula I (i.e., pregabalin), which have industrial applicability. For example, processes of the present invention avoid the use of bromine and produce pregabalin in high yield and with a low content of undesired by-products. In some embodiments, the present invention provides a process for preparing pregabalin of Formula I by reacting (R)-(−)-3-(carbamoylmethyl)-5-methylhexanoic acid of Formula II with sodium hypochlorite. In other embodiments, the present invention also provides pregabalin substantially free of impurities and pharmaceutical formulations comprising pregabalin.

DETAILED DESCRIPTION OF THE INVENTION

In some embodiments, the present invention provides processes for preparing pregabalin of Formula I:

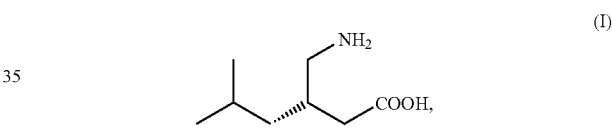

said processes comprising reacting (R)-(−)-3-(carbamoylmethyl)-5-methylhexanoic acid of Formula II:

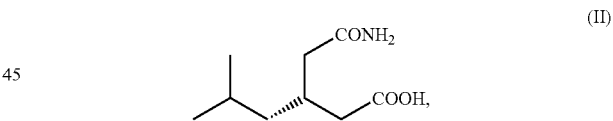

with sodium hypochlorite.

Sodium hypochlorite is used in processes of the present invention to convert (R)-(−)-3-(carbamoylmethyl)-5-methylhexanoic acid of Formula II to pregabalin of Formula I. Applicants have surprisingly discovered that, in contrast to the teachings of Hoekstra et al. in *Organic Process Research & Development* 1997, 1, 26-38, the Hofmann rearrangement of a compound of Formula II results in high yields of pregabalin when using sodium hypochlorite instead of bromine. Since sodium hypochlorite is cheaper and easier to handle than bromine, processes of the present invention are suitable for industrial scale.

Processes of the present invention are conducted in a suitable solvent, including mixtures of solvents. Typically, solvents in accordance with the invention comprise water. In some embodiments, the present invention provides processes for preparing pregabalin of Formula I from (R)-(−)-3-(carbamoylmethyl)-5-methylhexanoic acid of Formula II using sodium hypochlorite wherein the solvent comprises water.

In other embodiments, the present invention provides processes for preparing pregabalin from a compound of Formula II using sodium hypochlorite wherein the reaction is carried out in the presence of an alkaline hydroxide. In preferred embodiments, the alkaline hydroxide is sodium hydroxide.

In preferred embodiments, the reaction of (R)-(−)-3-(carbamoylmethyl)-5-methylhexanoic acid of Formula II with sodium hypochlorite to form pregabalin is carried out in a mixture of water and sodium hydroxide.

Applicants have surprisingly discovered that both (i) using a definite number of molar equivalents of sodium hypochlorite (e.g, less than about 1.3 molar equivalents), and (ii) carrying out the reaction at a temperature of about 50° C. to about 70° C., have an independent and complementary effect in the improvement of the Hofmann rearrangement reaction of the compound of Formula II to afford pregabalin of Formula I efficiently and with a low content of impurities, especially impurities having a HPLC relative retention time of 1.3. Therefore, the process described above is suitable for industrial implementation, since the process avoids the use of bromine, and provides pregabalin in good yields and with a low content of undesired by-products.

Applicants have discovered that regulating the temperature of the reaction in which a compound of Formula II is converted to a compound of Formula I using sodium hypochlorite provides unexpected benefits. For example, when a compound of Formula II is subjected to Hofmann rearrangement conditions using sodium hypochlorite at a temperature of about 40° C. to about 50° C., a significant amount of an undesired impurity is formed having a HPLC relative retention time of 1.3 when using the HPLC conditions described herein. This impurity remains even after multiple recrystallizations and is present in unacceptable concentrations for pharmaceutical applications.

In contrast, when a compound of Formula II is subjected to Hofmann rearrangement conditions using sodium hypochlorite at a temperature of about 50° C. to about 70° C., the amount of impurities having a HPLC relative retention time of 1.3 using the HPLC conditions described herein is decreased to almost undetectable levels, and in some cases, the impurities are decreased to undetectable levels.

Thus, in keeping with the invention, the reaction temperature and reaction conditions are selected to achieve low or even undetectable levels of impurities with a relative retention time of 1.3.

In an embodiment, the present invention provides a process for preparing pregabalin of Formula I, said process comprising reacting (R)-(−)-3-(carbamoylmethyl)-5-methylhexanoic acid of Formula II with sodium hypochlorite at a temperature of from about 50° C. to about 70° C.

Typically, the temperature at which processes of the invention are conducted range from about 50° C. to about 70° C. In preferred embodiments, processes of the present invention are conducted at a temperature of about 60° C.

In some embodiments, processes of the present invention comprise the step of contacting a compound of Formula II with sodium hypochlorite at a temperature of about 5° C. to about 10° C. prior to the reaction at a temperature of from about 50° C. to about 70° C., preferably to about 60° C. The reaction of sodium hypochlorite with a compound of Formula II is exothermic. Thus, in keeping with the invention, when sodium hypochlorite is added to a compound of Formula II at a temperature of about 5° C. to about 10° C., the sodium hypochlorite is added over a period of time such that the reaction mixture is maintained at a temperature of about 5° C. to about 10° C.

Applicants have surprisingly discovered that regulating the amount of sodium hypochlorite used in the conversion of a compound of Formula II to a compound of Formula (I) in accordance with the present invention has unexpected benefits. For example, when a compound of Formula II undergoes a Hofmann rearrangement in the presence of less than about 1.3 molar equivalents of sodium hypochlorite, the yield of pregabalin from the reaction unexpectedly increases from about 60% to about 70%.

In an embodiment, the present invention provides a process for preparing pregabalin of Formula I, said process comprising reacting (R)-(+3-(carbamoylmethyl)-5-methylhexanoic acid of Formula II with less than about 1.3 molar equivalents of sodium hypochlorite.

Typically, processes of the invention use less than about 1.3 molar equivalents of sodium hypochlorite. In preferred embodiments, the amount of sodium hypochlorite used is from about 0.90 molar equivalents to about 1.1 molar equivalents, most preferably the amount of sodium hypochlorite used is about 0.95 molar equivalents.

In other preferred embodiments, the present invention provides a process for preparing pregabalin of Formula I, said process comprising reacting (R)-(−)-3-(carbamoylmethyl)-5-methylhexanoic acid of Formula II (i) with less than about 1.3 molar equivalents of sodium hypochlorite, and (ii) at a temperature of from about 50° C. to about 70° C. Accordingly, in these embodiments, the amount of sodium hypochlorite and the temperature can be varied as described above. For example, the reaction is preferably conducted at 60° C. and the amount of sodium hypochlorite is preferably from about 0.90 molar equivalents to about 1.1 molar equivalents, most preferably the amount of sodium hypochlorite used is about 0.95 molar equivalents.

In some embodiments, processes of the present invention comprise the step of isolating pregabalin by treating the reaction mixture while at a temperature of about 30° C. to about 35° C. with a mineral acid to achieve a pH of about 5.0 to about 5.5.

In some embodiments, processes of the present invention comprise the step of crystallizing the pregabalin from a mixture of isopropanol and water.

In some embodiments, the present invention provides pregabalin of Formula I prepared according to processes of the invention. For example, in some embodiments the present invention provides pregabalin of Formula I which is prepared by reacting (R)-(+3-(carbamoylmethyl)-5-methylhexanoic acid of Formula II with sodium hypochlorite at a temperature of from about 50° C. to about 70° C., preferably about 60° C.

In other embodiments, the present invention provides pregabalin of Formula I which is prepared by reacting (R)-(−)-3-(carbamoylmethyl)-5-methylhexanoic acid of Formula II with less than about 1.3 molar equivalents of sodium hypochlorite, preferably from about 0.90 molar equivalents to about 1.1 molar equivalents of sodium hypochlorite, and most preferably about 0.95 molar equivalents of sodium hypochlorite.

In other embodiments, the present invention provides pregabalin of Formula I which is prepared by reacting (R)-(−)-3-(carbamoylmethyl)-5-methylhexanoic acid of Formula II with sodium hypochlorite wherein both the reaction temperature and amount of sodium hypochlorite is regulated as described herein.

Typically, pregabalin in accordance with the present invention is substantially free of impurities having an HPLC relative retention time of 1.3.

The HPLC conditions described herein in the Examples are illustrative of one method for determining impurities resulting from the process of the invention. Thus, in keeping with aspects of the present invention, HPLC is used to ascertain the purity of pregabalin, including analyzing pregabalin produced using processes of the invention for the presence of impurities which have a HPLC relative retention time of 1.3. In a particularly preferred embodiment, the following HPLC conditions are used to analyze pregabalin. A two-component mobile phase (A:B) is prepared by mixing (approximately) 76 volumes of mobile phase A and 24 volumes of mobile phase B. Component A is prepared by dissolving 0.58 g of monobasic ammonium phosphate and 1.83 g of sodium perchlorate in 1000 g of water and adjusting the pH to 1.8 with perchloric acid. Component B is acetonitrile. Samples of pregabalin are prepared in mobile phase A and chromatographed using a reverse-phase column equipped with UV detection monitoring at 215 nm.

Typically, pregabalin in accordance with the present invention comprises less than about 0.5% of an impurity having an HPLC relative retention time of 1.3 using the HPLC conditions described herein. In some embodiments, pregabalin of the present invention comprises less than about 0.25% of said impurities. In particularly preferred embodiments, pregabalin of the present invention has less than 0.1% of said impurities, most preferably no impurities having a HPLC relative retention time of 1.3 are detected using the HPLC conditions described herein.

In other embodiments, the present invention provides pharmaceutical formulations comprising pregabalin prepared according to processes of the invention, alone or in combination with other suitable ingredients (e.g., excipients or other active ingredients).

The following examples further illustrate the invention but, of course, should not be construed as in any way limiting its scope.

EXAMPLES

The following HPLC method was used to determine the presence of impurities. A two-component mobile phase (A:B) was prepared by mixing 76 volumes of mobile phase A and 24 volumes of mobile phase B, wherein component A was prepared by dissolving 0.58 g of monobasic ammonium phosphate and 1.83 g of sodium perchlorate in 1000 g of water, adjusting the pH to 1.8 with perchloric acid, filtering and degassing; component B was acetonitrile. Samples of pregabalin (30 µL, 20 mg/mL) were prepared using mobile phase A and chromatographed at ambient temperature using a Symmetry C18 column (5 µm; 250×4.6 mm) equipped with UV detection monitoring at 215 nm at a flow rate of 0.6 mL/min. The chromatogram was run for at least 40 min in isocratic mode.

Approximate HPLC retention times and relative retention times of pregabalin and an impurity are depicted in the table below.

| Compound | Retention Time (minutes) | Relative Retention Time (RRT) |
| --- | --- | --- |
| Pregabalin | 6.8 | 1 |
| Impurity | 9.1 | 1.3 |

Example 1

This example illustrates a process for preparing (S)-(+)-3-aminomethyl-5-methyl-1-hexanoic acid (i.e., pregabalin of Formula I) in accordance with an embodiment of the invention.

In a 1 L, four-neck, round-bottom reaction vessel, purged with nitrogen and equipped with a reflux condenser, 500 mL pressure-equalized addition funnel, thermometer and blade impeller, were added in sequence 47.38 g (0.253 mol) of compound of Formula II and 56.85 g of water.

The mixture was stirred to give a thick suspension and cooled to 5-10° C.

24.07 g (0.301 mol, 1.2 molar eq.) of 50% w/w sodium hydroxide solution were added dropwise onto the stirred suspension over a period of about 25 min, maintaining the temperature at 5-10° C. Once addition was complete, the mixture was stirred for an additional 20 minutes.

In a separate 500 mL, three neck, round-bottom reaction vessel, purged with nitrogen and equipped with a blade impeller, were added in sequence 274.23 g (0.329 mol, 1.3 molar eq.) of 8.93% w/w aqueous sodium hypochlorite solution, 22.74 g of water and 34.12 g of 50% w/w aqueous sodium hydroxide.

The basic hypochlorite solution thus prepared was added dropwise from an addition funnel to the aqueous solution of compound of Formula II while maintaining the temperature at 5-10° C.

Once addition was complete, cooling was removed and the reaction was allowed to warm up while stirring. A spontaneous exothermic reaction initiated at around 25° C., raising the reaction temperature to 40-50° C. Once the exothermicity subsided, the reaction mixture was heated to a temperature of 40-50° C. for 1 h, applying heat as necessary to maintain the temperature.

After this period of heating, the reaction mixture was cooled to 30-35° C.

While maintaining the temperature at 30-35° C., about 82 g of 35% w/w aqueous hydrochloric acid were added until a pH of 5.0-5.5 was achieved. A peach-coloured suspension was observed to form during the addition.

The suspension was then cooled to 5-10° C. and stirred at this temperature for 1 h.

The suspension was filtered and the collected solid was washed with 23.69 g of cold 5% w/w aqueous sodium chloride solution followed by 23.69 g of cold water to yield 27.93 g of wet, pale orange, crude pregabalin (LOD: 14.95%, estimated dry mass: 23.75 g, yield: 58.9%).

In a 1 L, four-neck, round-bottom reaction vessel, purged with nitrogen and equipped with a reflux condenser, 500 mL pressure-equalized addition funnel, thermometer and blade impeller, were added in sequence 24.44 g of the wet crude pregabalin obtained in the previous step (estimated dry mass: 20.79 g), 81.60 g of isopropanol and 62.37 g of water.

The suspension was heated to reflux until complete dissolution occurred. A yellow solution was thus obtained. The solution was cooled to 5-10° C. and then stirred at this temperature for 1 h.

The suspension was filtered and the collected solid was washed with 16.32 g of isopropanol to yield 18.53 g of wet, white pregabalin (LOD: 4.35%, estimated dry mass: 17.72 g, yield: 85.2%).

Chromatographic purity (HPLC): pregabalin: 99.03%, impurity RRT 1.3: 0.22%.

In a 1 L, four neck, round-bottom reaction vessel, purged with nitrogen and equipped with a reflux condenser, 500 mL pressure-equalized addition funnel, thermometer and blade impeller, were added in sequence 15.46 g of wet pregabalin from the previous step (estimated dry mass: 14.79 g), 58.01 g of isopropanol and 51.73 g of water.

The suspension was heated to reflux until complete dissolution occurred. A yellow solution was thus obtained. The solution was cooled to 75-80° C. and filtered to remove insoluble particles. The solution was cooled further to 5-10° C. and then stirred at this temperature for 1 h.

The suspension was filtered and the collected solid was washed with 11.61 g of isopropanol to yield 13.36 g of wet, white pregabalin.

The wet solid was dried at 60° C. under vacuum for 4 h to give 13.11 g of dry, white pregabalin (LOD: 0.08%, yield: 88.6%).

Chromatographic purity (HPLC): pregabalin: 99.37%, impurity RRT 1.3: 0.19%.

These results demonstrate that a process in accordance with the invention can produce pregabalin of Formula I in high yield substantially free of impurities having a HPLC relative retention time of 1.3, wherein said impurities are present in less than about 0.20%.

Example 2

This example illustrates a process for preparing (5)-(+)-3-aminomethyl-5-methyl-1-hexanoic acid (i.e., pregabalin of Formula I) in accordance with an embodiment of the invention.

In a 1 L, four neck, round-bottom reaction vessel, purged with nitrogen and equipped with a reflux condenser, 500 mL pressure-equalized addition funnel, thermometer and blade impeller, were added in sequence 29.08 g (0.155 mol) of compound of Formula II and 34.90 g of water. The mixture was stirred to give a thick suspension and cooled to 5-10° C.

14.91 g (0.186 mol, 1.2 molar eq.) of 50% w/w sodium hydroxide solution were added dropwise onto the stirred suspension over a period of about 25 min, maintaining the temperature at 5-10° C. Once addition was complete, the mixture was stirred for an additional 20 min.

In a separate 500 mL, three neck, round-bottom reaction vessel, purged with nitrogen and equipped with a blade impeller, were added in sequence 144.02 g (0.171 mol, 1.1 molar eq.) of 8.83% w/w aqueous sodium hypochlorite solution, 13.95 g of water and 20.94 g of 50% w/w aqueous sodium hydroxide.

The basic hypochlorite solution thus prepared was added dropwise from an addition funnel to the aqueous solution of compound of Formula II while maintaining the temperature at 5-10° C.

Once addition was complete, cooling was removed and the reaction was allowed to warm up while stirring. A spontaneous exothermic reaction initiated at around 25° C., raising the reaction temperature to 49° C. Once the exothermicity subsided, the reaction mixture was heated to a temperature of 45-50° C. for 1 h, applying heat as necessary to maintain the temperature.

After this period of heating, the reaction mixture was cooled to 30-35° C.

While maintaining the temperature at 30-35° C., about 50 g of 35% w/w aqueous hydrochloric acid were added until a pH of 5.0-5.5 was achieved. A peach-coloured suspension was observed to form during the addition.

The suspension was then cooled to 5-10° C. and stirred at this temperature for 1 h.

The suspension was filtered and the collected solid was washed with 14.54 g of cold 5% w/w aqueous sodium chloride solution followed by 14.54 g of cold water to yield 20.19 g of wet, pale orange, crude pregabalin (LOD: 14.51%, estimated dry mass: 17.26 g, yield: 69.8%).

In a 1 L, four neck, round-bottom reaction vessel, purged with nitrogen and equipped with a reflux condenser, 500 mL pressure-equalized addition funnel, thermometer and blade impeller, were added in sequence 18.09 g of wet pregabalin from the previous step (estimated dry mass: 15.47 g), 60.72 g of isopropanol and 54.15 g of water.

The suspension was heated to reflux until complete dissolution occurred. A yellow solution was thus obtained. The solution was cooled further to 5-10° C. and then stirred at this temperature for 1 h.

The suspension was filtered and the collected solid was washed with 5.5 g of water and 5.6 g of isopropanol to yield 14.49 g of wet, white pregabalin (LOD: 9.57%, estimated dry mass: 13.10 g, yield: 84.7%).

Chromatographic purity (HPLC): pregabalin: 99.45%, impurity RRT 1.3: 0.21%.

In a 1 L, four-neck, round-bottom reaction vessel, purged with nitrogen and equipped with a reflux condenser, 500 mL pressure-equalized addition funnel, thermometer and blade impeller, were added in sequence 12.47 g of wet crude pregabalin from the previous stage (estimated dry mass: 11.28 g), 44.27 g of isopropanol and 56.39 g of water.

The suspension was heated to reflux until complete dissolution occurred. A yellow solution was thus obtained. The solution was cooled to 5-10° C. and then stirred at this temperature for 1 h.

The suspension was filtered and the collected solid was washed with 4.7 g of water 4.8 g of isopropanol to yield 10.66 g of wet, white pregabalin.

The wet solid was dried at 60° C. under vacuum for 4 h to give 9.48 g of dry, white pregabalin (LOD: 11.07%, yield: 84.0%).

Chromatographic purity (HPLC): pregabalin: 99.63%, impurity RRT 1.3: 0.17%.

These results demonstrate that a process in accordance with the invention can produce pregabalin of Formula I in high yield substantially free of impurities having a HPLC relative retention time of 1.3, wherein said impurities are present in less than about 0.20%.

Example 3

This example illustrates a process for preparing (S)-(+)-3-aminomethyl-5-methyl-1-hexanoic acid (i.e., pregabalin of Formula I) in accordance with an embodiment of the invention.

In a 1 L, four-neck, round-bottom reaction vessel, purged with nitrogen and equipped with a reflux condenser, 500 mL pressure-equalized addition funnel, thermometer and blade impeller, were added in sequence 12.00 g (0.064 mol) of compound of Formula II and 14.4 g of water.

The mixture was stirred to give a thick suspension and cooled to 5-10° C.

6.15 g (0.077 mol, 1.2 molar eq.) of 50% w/w sodium hydroxide solution were added dropwise onto the stirred suspension over a period of about 20 min, maintaining the temperature at 5-10° C. Once addition was complete, the mixture was stirred for an additional 20 min.

In a separate 500 mL, three-neck, round-bottom reaction vessel, purged with nitrogen and equipped with a blade impeller, were added in sequence 70.24 g (0.083 mol, 1.3 molar eq.) of 8.83% w/w aqueous sodium hypochlorite solution, 5.76 g of water and 8.64 g of 50% w/w aqueous sodium hydroxide.

The basic hypochlorite solution thus prepared was added dropwise from an addition funnel to the aqueous solution of compound of Formula II while maintaining the temperature at 5-10° C.

Once addition was complete, cooling was removed and the reaction was allowed to warm up while stirring. A spontaneous exothermic reaction initiated at around 25° C., raising the reaction temperature to about 40° C. Once the exothermicity subsided, the reaction mixture was heated to a temperature of 70±2° C. for 1 h, applying heat as necessary to maintain the temperature.

After this period of heating, the reaction mixture was cooled to 30-35° C.

While maintaining the temperature at 30-35° C., about 21 g of 35% w/w aqueous hydrochloric acid were added until a pH of 5.0-5.5 was achieved. A peach-coloured suspension was observed to fatal during the addition.

The suspension was then cooled to 5-10° C. and stirred at this temperature for 1 h.

The suspension was filtered and the collected solid was washed with 6.00 g of cold 5% w/w aqueous sodium chloride solution followed by 6.00 g of cold water to yield 6.94 g of wet, pale orange, crude pregabalin (LOD: 14.44%, estimated dry mass: 5.94 g, yield: 58.2%).

In a 1 L, four-neck, round-bottom reaction vessel, purged with nitrogen and equipped with a reflux condenser, 500 mL pressure-equalized addition funnel, thermometer and blade impeller, were added in sequence 5.84 g of wet crude pregabalin from the previous stage (estimated dry mass: 4.99 g), 19.59 g of isopropanol and 17.47 g of water.

The suspension was heated to reflux until complete dissolution occurred. A yellow solution was thus obtained. The solution was cooled to 5-10° C. and then stirred at this temperature for 1 h.

The suspension was filtered and the collected solid was washed with 1.77 g of water and 1.80 g of isopropanol to yield 4.27 g of wet, white pregabalin.

The wet solid was dried at 60° C. under vacuum to give 4.18 g of dry, white pregabalin (LOD: 2.00%, yield: 83.9%).

Chromatographic purity (HPLC): pregabalin: 99.26%, impurity RRT 1.3: 0.01%.

These results demonstrate that a process in accordance with the invention can produce pregabalin of Formula I in high yield substantially free of impurities having a HPLC relative retention time of 1.3, wherein said impurities are present in 0.01% after only a single crystallization from a mixture of isopropanol and water.

Example 4

This example illustrates a process for preparing (S)-(+)-3-aminomethyl-5-methyl-1-hexanoic acid (i.e., pregabalin of Formula I) in accordance with an embodiment of the invention.

In a 1 L, four neck, round-bottom reaction vessel, purged with nitrogen and equipped with a reflux condenser, 500 mL pressure-equalized addition funnel, thermometer and blade impeller, were added in sequence 56.38 g (0.301 mol) of compound of Formula II and 67.66 g of water. The mixture was stirred to give a thick suspension and cooled to 5-10° C.

28.92 g (0.362 mol, 1.2 molar eq.) of 50% w/w sodium hydroxide solution were added dropwise onto the stirred suspension over a period of about 25 min, maintaining the temperature at 5-10° C. Once addition was complete, the mixture was stirred for an additional 20 min.

In a separate 500 mL, three necked, round-bottomed reaction vessel, purged with nitrogen and equipped with a blade impeller, were added in sequence 206.90 g (0.316 mol, 1.05 molar eq.) of 11.38% w/w aqueous sodium hypochlorite solution, 27.06 g of water and 40.59 g of 50% w/w aqueous sodium hydroxide.

The basic hypochlorite solution thus prepared was added dropwise from an addition funnel to the aqueous solution of compound of Formula II while maintaining the temperature at 5-10° C.

Once addition was complete, cooling was removed and the reaction was allowed to warm up while stirring. A spontaneous exothermic reaction initiated at around 25° C., raising the reaction temperature to 40-50° C. Once the exothermicity subsided, the reaction mixture was heated to a temperature of 60±2° C. for 1 h, applying heat as necessary to maintain the temperature.

After this period of heating, the reaction mixture was cooled to 30-35° C. While maintaining the temperature at 30-35° C., about 92 g of 35% w/w aqueous hydrochloric acid were added until a pH of 5.0-5.5 was achieved. A peach-coloured suspension was observed to form during the addition.

The suspension was then cooled to 5-10° C. and stirred at this temperature for 1 h.

The suspension was filtered and the collected solid was washed with 28.19 g of cold 5% w/w aqueous sodium chloride solution followed by 28.19 g of cold water to yield 41.04 g of wet, pale orange, crude pregabalin (LOD: 12.44%, estimated dry mass: 35.93 g, estimated yield: 74.9%).

In a 1 L, four neck, round-bottom reaction vessel, purged with nitrogen and equipped with a reflux condenser, 500 mL pressure-equalized addition funnel, thermometer and blade impeller, were added in sequence 41.04 g of the wet pregabalin from the previous step (estimated dry mass: 35.93 g), 141.03 g of isopropanol and 125.76 g of water.

The suspension was heated to reflux until complete dissolution occurred. A yellow solution was thus obtained. The solution was cooled to 75-80° C. and filtered to remove insoluble particles. The solution was cooled further to 5-10° C. and then stirred at this temperature for 1 h.

The suspension was filtered and the collected solid was washed with 28.21 g of isopropanol to yield 32.35 g of wet, white pregabalin.

The wet solid was dried at 60° C. under vacuum for 4 h to give 30.13 g of dry, white pregabalin (LOD: 6.87%, yield: 83.9%).

Chromatographic purity (HPLC): pregabalin: 99.63%, impurity RRT 1.3: Not detected.

These results demonstrate that a process in accordance with the invention can produce pregabalin of Formula I in high yield substantially free of impurities having a HPLC relative retention time of 1.3, such that said impurities are not detectable by HPLC after only a single crystallization from a mixture of isopropanol and water.

Example 5

This example illustrates a process for preparing (S)-(+)-3-aminomethyl-5-methyl-1-hexanoic acid (i.e., pregabalin of Formula I) in accordance with an embodiment of the invention.

In a 1 L, four-necked, round-bottom reaction vessel, purged with nitrogen and equipped with a reflux condenser, 500 mL pressure-equalized addition funnel, thermometer, and blade impeller, were added in sequence 43.16 g (0.231 mol) of compound of Formula II and 51.79 g of water. The mixture was stirred to give a thick suspension and cooled to 5-10° C.

22.13 g (0.277 mol, 1.2 molar eq.) of 50% w/w sodium hydroxide solution was added dropwise onto the stirred suspension over a period of about 30 min, maintaining the temperature at 5-10° C. Once addition was complete, the mixture was stirred for a further 30 min.

In a separate 250 mL, three-necked, round-bottomed reaction vessel, purged with nitrogen and equipped with a blade impeller, were added in sequence at 5-10° C. 158.57 g (0.219 mol, 0.95 molar eq.) of 10.28% w/w aqueous sodium hypochlorite solution, 20.72 g of water and 31.08 g of 50% w/w aqueous sodium hydroxide.

The basic hypochlorite solution thus prepared was added dropwise from an addition funnel to the aqueous solution of compound of Formula II, while maintaining the temperature at 5-10° C.

Once addition was complete, cooling was removed and the reaction was allowed to warm while stirring. A spontaneous exothermic reaction initiated at around 25° C., raising the reaction temperature to 40-50° C. Once the exothermicity subsided, the reaction mixture was heated to a temperature of 60±2° C. for 1 h, applying heat as necessary to maintain the temperature.

After this period of heating, the reaction mixture was cooled to 30-35° C. While maintaining the temperature at 30-35° C., about 70 g of 35% w/w aqueous hydrochloric acid were added until a pH of 5.0-5.5 was achieved. A peach-coloured suspension was observed to form during the addition.

The suspension was then cooled to 5-10° C. and stirred at this temperature for 1 h.

The suspension was filtered and the collected solid was washed with 25.0 g of cold water followed by 19.63 g of cold isopropanol to yield 30.64 g of wet, peach-coloured crude pregabalin (LOD: 2.00%, estimated dry mass: 30.03 g, yield: 81.8%).

Chromatographic purity (HPLC): pregabalin: 98.42%, impurity RRT 1.3: 0.01%.

In a 500 mL, four-necked, round-bottomed reaction vessel, purged with nitrogen and equipped with a reflux condenser, thermometer, and blade impeller, are added in sequence 30.64 g of the wet pregabalin of the previous step (estimated dry mass: 30.03 g), 117.87 g of isopropanol and 105.11 g of water.

The suspension was heated to reflux until complete dissolution occurred. The solution was cooled to 5-10° C. and then stirred at this temperature for 1 h.

The suspension was filtered and the collected solid was washed with a mixture of 12.97 g of isopropanol and 12.90 g of water to yield 27.09 g of wet, off-white pregabalin (LOD: 1.56%, estimated dry mass: 26.67 g, yield: 88.8%).

Chromatographic purity (HPLC): pregabalin: 99.79%, impurity RRT 1.3: 0.01%.

In a 500 mL, four-necked, round-bottomed reaction vessel, purged with nitrogen and equipped with a reflux condenser, thermometer, and blade impeller, are added in sequence 27.09 g of wet crude pregabalin from the previous stage (estimated dry mass: 26.67 g), 104.68 g of isopropanol and 93.35 g of water.

The suspension was heated to reflux until complete dissolution occurred. The solution was cooled down to 75-80° C. and filtered to remove insoluble particles. The solution was cooled further to 5-10° C. and then stirred at this temperature for 1 h.

The suspension was filtered and the collected solid is washed with a mixture of 11.52 g of isopropanol and 11.46 g of water to yield 25.50 g of wet, white pregabalin.

The wet solid was dried at 60° C. under vacuum for 4 h to give 23.92 g of dry, white pregabalin (LOD: 6.19%, yield: 89.7%).

Chromatographic purity (HPLC): pregabalin: 99.80%, impurity RRT 1.3: Not detected.

These results demonstrate that a process in accordance with the invention can produce pregabalin of Formula I in high yield substantially free of impurities having a HPLC relative retention time of 1.3, such that said impurities are not detectable by HPLC after only two crystallizations from a mixture of isopropanol and water.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A process for preparing pregabalin of Formula I:

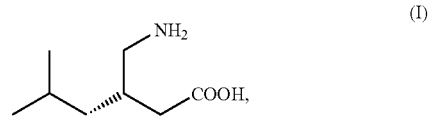

said process comprising reacting (R)-(−)-3-(carbamoylmethyl)-5-methylhexanoic of Formula II:

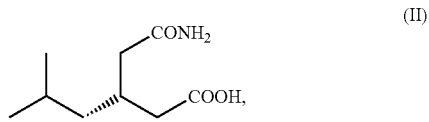

with sodium hypochlorite at a temperature of from about 50° C. to about 70° C.

2. The process of claim 1, wherein the temperature is about 60° C.

3. The process of claim 1, wherein the amount of sodium hypochlorite is less than about 1.3 molar equivalents.

4. The process of claim 3, wherein the amount of sodium hypochlorite is from about 0.90 molar equivalents to about 1.1 molar equivalents.

5. The process of claim 4, wherein the amount of sodium hypochlorite is about 0.95 molar equivalents.

6. The process of claim 1, wherein the reaction is carried out in a solvent comprising water.

7. The process of claim 1, wherein the reaction is carried out in the presence of an alkaline hydroxide.

8. The process of claim 6, wherein the reaction is carried out in the presence of an alkaline hydroxide.

9. The process of claim 7, wherein the alkaline hydroxide is sodium hydroxide.

10. The process of claim 8, wherein the alkaline hydroxide is sodium hydroxide.

11. The process of claim 1 further comprising the step of contacting compound of Formula II with sodium hypochlorite at a temperature of from about 5° C. to about 10° C. prior to the reaction at a temperature of from about 50° C. to about 70° C.

12. The process of claim 1 further comprising the step of isolating pregabalin by treating the reaction mixture while at a temperature of about 30° C. to about 35° C. with a mineral acid to achieve a pH of about 5.0 to about 5.5.

13. The process of claim 1 further comprising the step of crystallizing the obtained pregabalin from a mixture of isopropanol and water.

* * * * *